(12) United States Patent
Kelley et al.

(10) Patent No.: US 11,986,383 B1
(45) Date of Patent: May 21, 2024

(54) DELIVERY SYSTEMS FOR INSERTING DEVICES INTO BODY LUMENS

(71) Applicants: Scott T. Kelley, Tampa, FL (US); Jill Kelley, Tampa, FL (US)

(72) Inventors: Scott T. Kelley, Tampa, FL (US); Jill Kelley, Tampa, FL (US)

(73) Assignee: SAFEGUARD SURGICAL, INC., Tampa, FL (US)

( * ) Notice: Subject to any disclaimer, the term of this patent is extended or adjusted under 35 U.S.C. 154(b) by 0 days.

(21) Appl. No.: 18/232,902

(22) Filed: Aug. 11, 2023

Related U.S. Application Data

(60) Provisional application No. 63/523,129, filed on Jun. 26, 2023.

(51) Int. Cl.
*A61F 2/04* (2013.01)

(52) U.S. Cl.
CPC .......... *A61F 2/04* (2013.01); *A61F 2002/045* (2013.01); *A61F 2220/005* (2013.01)

(58) Field of Classification Search
CPC . A61F 2/04; A61F 2002/045; A61F 2220/005
See application file for complete search history.

(56) References Cited

U.S. PATENT DOCUMENTS

| | | | | |
|---|---|---|---|---|
| 5,180,392 A | * | 1/1993 | Skeie | A61B 17/1114 606/155 |
| 8,663,086 B2 | * | 3/2014 | Duncan | A61F 2/0036 600/30 |
| 8,894,699 B2 | * | 11/2014 | Kelley | A61F 2/04 606/154 |
| 9,827,135 B2 | * | 11/2017 | Fong | A61F 5/449 |
| 2007/0100420 A1 | * | 5/2007 | Kavanagh | A61B 17/1204 623/1.11 |
| 2008/0255650 A1 | * | 10/2008 | Kelley | A61B 17/1114 623/1.42 |
| 2009/0281634 A1 | * | 11/2009 | Abell | A61F 2/04 623/23.65 |
| 2011/0319902 A1 | * | 12/2011 | Epstein | A61M 25/01 606/108 |
| 2020/0155338 A1 | * | 5/2020 | Meteer | A61F 5/443 |
| 2023/0087452 A1 | * | 3/2023 | Gilmartin | A61F 5/0076 604/8 |
| 2023/0255722 A1 | * | 8/2023 | Saenz Villalobos | A61B 90/39 606/155 |

\* cited by examiner

*Primary Examiner* — Suzette J Gherbi
(74) *Attorney, Agent, or Firm* — Law Office of Vincent LoTempio PLLC; Vincent G. LoTempio; Robert L. Cerasa

(57) ABSTRACT

Systems and methods to prevent leakage of an intestine and/or provide support to an intestine. The systems can carry the leakage protection device on an external surface for delivery or carry the leakage protection device internally within a lumen. The device is delivered into the intestine portions to protect a site where a defect is repaired such as at an anastomotic site.

17 Claims, 12 Drawing Sheets

DELIVERY SYSTEMS FOR INSERTING DEVICES INTO BODY LUMENS

CROSS REFERENCE OF RELATED APPLICATIONS

This application claims the benefits of U.S. provisional application No. 63/523,129 filed Jun. 26, 2023 and entitled "DELIVERY SYSTEMS FOR INSERTING DEVICES INTO BODY LUMENS", which provisional application is incorporated by reference herein in its entirety.

FIELD OF THE INVENTION

This application is directed to devices for insertion into body lumens to provide protection from leakage during and/or after surgical procedures, to provide support to the body lumens after surgical procedures and/or seal a perforation.

BACKGROUND OF THE INVENTION

The gastrointestinal (GI) tract extends from the esophagus to the anus and serves many functions, including nutrition, hydration, and disease prevention. Resection of a portion of the GI tract, such as esophagus, stomach, small intestine, large intestine or colon, is performed on a patient under general anesthesia. An incision is typically made in the abdomen, chest or neck and a diseased portion is removed. The healthy ends that remain are sewn or stapled together and the incision is closed through the procedure known as anastomosis. There is substantial risk of the patient leaking at the site of the anastomosis even if the surgeon follows best practices. Leakage may lead to contamination of the peritoneal or thoracic cavity, sepsis and even death. Leakage may be evident immediately or it may be delayed at the site of anastomosis, regardless of the skill of the surgeon.

Although research to decrease failure rates of resection/anastomosis has been considerable, success has been elusive. Advances in minimally invasive procedures allow surgeons to perform resection and anastomosis using laparoscopic or thoracoscopic technologies. However, many surgeons are unwilling to use less invasive procedures due to the inherent risks of leakage and severity of the complications of leakage from the GI tract. As an alternative to connecting the two intestinal ends or to protect the newly created anastomosis, the surgeon may perform an ostomy or stoma, exteriorizing a portion of the intestine and leaving a patient with an opening on the abdomen or neck. Such procedures, however, involve having the patient wear an external pouch to collect intestinal waste. Possible infection and restrictions on patient lifestyles make this option unattractive. If an anastomosed site leaks, then a surgeon often opts to perform an ostomy as a necessity to prevent any further sepsis, morbidity or death of the patient.

It would be advantageous to provide a device to reduce risks of leakage at the anastomotic site.

In some procedures, the surgeon utilizes a temporary colostomy bag to protect the anastomotic site from contact with the stool post surgery. It would be advantageous to provide a device to protect the area to avoid the need for such colostomy bags.

It would also be advantageous to provide a device to close off perforations in intestines or body lumens.

Further, the need exists for delivery systems to deliver such devices within the body lumens.

SUMMARY OF THE INVENTION

Commonly owned U.S. Pat. No. 8,894,699 (hereinafter the '699 patent) discloses devices which effectively addressed reducing the risk of leaks at the anastomotic site. The devices disclosed are in the form of a covered stent providing a scaffold. An impermeable layer is placed over and attached to the scaffold. The device is inserted between or into the lumen ends to be anastomosed to provide stability and/or structure to the anastomosed lumen.

The inventor of the '699 patent, along with the other inventor of the present application, conceived of modifications to the device of the '699 patent which could provide advantages in certain clinical applications, as well as conceived of new advantageous uses of the devices, which are described in detail below.

The inventor of the '699 patent, along with the other inventor of the present application, conceived of delivery systems to effectively deliver such devices within the body lumens. In some embodiments, the device is placed external of the delivery device and carried thereon to the anastomotic or other site. In other embodiments, the device is carried within an outer member sheath and exposed from the sheath adjacent the target site. Both types of systems are described in detail below.

The devices described herein can also be used to protect and/or support the lumens/tissue during and/or after treatment such as radiation such as disclosed in commonly owned provisional application Ser. No. 63/452,194, filed Mar. 15, 2023, the entire contents of which are incorporated herein by reference.

The devices described herein can also be used for insertion into or over body lumens for treating cancer as disclosed in commonly owned provisional application Ser. No. 63/452,197, filed Mar. 15, 2023, the entire contents of which are incorporated herein by reference.

In one aspect, the present invention provides a device in the form of a biodegradable tubular structure to provide support and stability for anastomosis of a lumen and/or reduce leakage at the anastomotic site. Sealant, such as an adhesive, can be utilized to attach the tubular structure to the body lumens.

In another aspect of the present invention, the biodegradable tubular device can be used to close off perforations of the intestine or other body lumens.

In another aspect of the present invention, the biodegradable tubular device can be used to support tissue during tissue treatments such a radiation.

In one aspect, the present invention provides a device in the form of a biodegradable tubular structure to provide support and stability for anastomosis of a lumen and/or reduce leakage at the anastomotic site. An adhesive can be utilized to attach the tubular structure to the body lumens and the adhesive can also provide a sealant. The device can be placed to prevent leaks, i.e., to prophylactically prevent leaks at the time of surgery rather than placed after a leak occurs. The tubular device of the present invention is in the form of a straw with a thin wall and a lumen extending therethrough, and has an open proximal and distal end to enable flow therethrough. The tubular device in some embodiments is shaped like a condom (with a rim/rib top) or can be a colon-shaped device. ("Top" referring to the portion/region closer to the head of the patient).

In another aspect of the present invention, the biodegradable tubular device can be used to close off perforations, tears, rips or ulcers of body lumens, such as the intestine, which need to be repaired or protected.

In another aspect of the present invention, the biodegradable tubular device can be used to close off leaks of the intestine or other body lumens if it develops after surgery.

In another aspect of the present invention, the tubular device can be made of tissue engineered material, e.g., from tissue generated organs, and placed in the colon to provide extra support to seal and prevent leakage.

In accordance with another aspect of the present invention, a method to prevent leakage in an intestine is provided comprising the steps of a) positioning a tubular straw like device in a lumen of the first intestine to be attached to the second intestine at an anastomotic site; and b) securing the device to the intestine utilizing an adhesive. The device can include a treatment or healing substance adhered thereto.

In accordance with another aspect of the present invention, a method to seal a perforation in a body lumen is provided comprising a) positioning a tubular straw like device in the body lumen, the device having a rim having an enlarged diameter to provide a radial force against the intestine; and b) securing the device to a wall of the body lumen utilizing an adhesive, the rim preventing backflow past the rim.

The methods utilize in some embodiments a tubular device having an enlarged rim providing a diameter larger than other regions of the device. The rim is at the top portion of the device and in some embodiments provides a radial force against the tissue, e.g., colon wall, to help secure the device in place. The device can be held in place by an adhesive. In preferred embodiments, the adhesive utilized has a dual function: adhering the device to the tissue, e.g., luminal wall, and providing a seal to prevent unwanted flow.

In accordance with another aspect of the present invention a device to limit leakage of a lumen is provided, the device comprising a tubular straw like body and having a rim, the device composed of a tissue engineered material and held in place at the rim by an adhesive.

In accordance with another aspect of the present invention, a device to limit leakage of a luminal region of a body of a patient is provided, the device comprising a tubular straw like configuration having an outer wall and an inner wall defining a lumen extending through the device, the device attachable to the region via adhesive.

The present invention also provides various delivery instruments and systems for the leakage protection devices of the present invention. Such instruments and systems can also be utilized with the other tubular devices described herein, e.g., used to support lumens, treating cancer, etc.

In accordance with an aspect of the present invention, a method to prevent leakage of an intestine and/or provide support to an intestine is provided comprising the steps of a) advancing an anastomotic instrument through a first intestine portion and a second intestine portion, the anastomotic instrument carrying a tubular straw like device on an outer wall of a shaft of the instrument, the tubular device formed as one piece and having a first end opening, a second end opening and a lumen extending through an entire length of the device; b) actuating the instrument to attach the first intestine portion to the second intestine portion to form an anastomotic site; c) after step b, advancing the tubular straw like device distally over the shaft of the instrument into a lumen of the first intestine portion and the second intestine portion; and d) securing the device to the first intestine portion such that an outer wall of the device extends across the anastomotic site. In some embodiments, the step of securing the device comprises the step of securing the device utilizing an adhesive.

In some embodiments, the device includes a treatment or healing substance adhered thereto.

In some embodiments, the anastomotic instrument comprises a stapling instrument deploying at least one annular array of staples. A pusher can be provided to advance the device over the shaft of the instrument.

In some embodiments, the method further comprises the step of centering a stapling head of the instrument at the anastomotic site and delivering the tubular straw like device so it is centered at the site. In some embodiments, one or both of the instrument or device have alignment markers to aid in centering the device.

The instrument can be used to deliver various devices. In some embodiments, the instrument delivers a device having a first diameter and a rim having a second diameter larger than the first diameter, and the adhesive is placed on the rim, the rim preventing backflow through the rim, the rim providing a radial force against the intestine. In some embodiments, the device is formed of tissue engineered material such as colon cells.

In accordance with another aspect of the present invention, a method to prevent leakage of an intestine or provide support to the intestine is provided comprising a) advancing an instrument through a first intestine portion and a second intestine portion, the instrument carrying a tubular straw like device on an outer wall of the instrument, the tubular device formed as one piece and having a first end opening, a second end opening and a lumen extending through an entire length of the device; b) advancing the tubular straw like device distally over the outer wall of the instrument into a lumen of the first intestine portion and the second intestine portion; and c) securing the device to the first intestine portion such that an outer wall of the device extends across the anastomotic site.

In some embodiments, the instrument is a proctoscope.

In some embodiments, the step of securing the device comprises the step of securing the device utilizing an adhesive.

In some embodiments, a pusher advances the device over the shaft of the instrument.

In accordance with another aspect of the present invention. a method to prevent leakage of an intestine or provide support to the intestine, is provided comprising a) advancing an instrument through a first intestine portion and a second intestine portion, the instrument having a lumen retaining a tubular straw like device therein, the tubular device formed as one piece and having a first end opening, a second end opening and a lumen extending through an entire length of the device; b) advancing the tubular straw like device through the lumen of the instrument exiting a distal end of the instrument and into a lumen of a first intestine portion and the second intestine portion; and c) securing the device to the first intestine portion such that an outer wall of the device extends across the anastomotic site.

In some embodiments, the instrument includes a pusher therein, the pusher is advanceable to advance the tubular device out of the lumen of the instrument.

In some embodiments, a distal tip of the instrument separates to enable passage of the device through the distal tip and into the first intestine.

In some embodiments, the device includes a string extending proximally thereof to enable retrieval of the device after delivery.

BRIEF DESCRIPTION OF THE DRAWINGS

So that those having ordinary skill in the art to which the subject invention appertains will more readily understand how to make and use the apparatus (device) disclosed herein, preferred embodiments thereof will be described in detail hereinbelow with reference to the drawings, wherein:

FIGS. 5 and 6 are perspective views of an alternate embodiment of the device of the present invention placed over the first and second intestine portions, wherein;

FIG. 5 shows the tubular device inserted over the first intestine portion, the second intestine portion not yet attached; and FIG. 6 shows the tubular device positioned over the first and second intestine portions and the second intestine portion placed in apposition (abutment) with the first intestine portion;

FIGS. 10-17 illustrate an embodiment of the delivery system of the present invention utilizing a circular stapler shown in use in the colon (with a side portion of the colon removed to illustrate the device in the lumen of the colon) wherein FIG. 10 illustrates the circular stapler carrying the leak protection device externally on the shaft, the stapler shown prior to insertion into the colon;

FIG. 11 illustrates the stapler being inserted into the colon with the leak prevention device remaining outside the colon;

FIG. 12 illustrates the stapler opened and positioned near the defect;

FIG. 13 illustrates the colon defect repaired with the stapler as the anvil is approximated and staples are applied;

FIG. 14 illustrates the device inserted further into the colon such that the stapler head is centered over the repaired defect;

FIG. 15 illustrates the leak preventing device advanced over the shaft of the stapler toward the site of the repaired defect;

FIG. 16 illustrates the leak prevention device centered at the site of the repaired defect; and FIG. 17 illustrates the stapler being removed from the patient leaving the leak prevention device at the site of the repaired defect.

FIGS. 19-21 illustrate an alternate embodiment of the delivery system of the present invention wherein FIG. 19 illustrates the leak protection device positioned and protected within an outer sheath;

FIG. 20 illustrates the leak protection device being advanced by the internal pusher out of the outer sheath; and FIG. 21 illustrates the leak protection device fully advanced from the sheath and the sheath and pusher being withdrawn.

DETAILED DESCRIPTION OF THE INVENTION

As noted above, commonly owned U.S. Pat. No. 8,894,699, incorporated herein by reference in its entirety, and having a common inventor with the present application, disclosed devices which effectively addressed leakage at the anastomotic site. The devices disclosed are in the form of a covered stent providing a scaffold inserted between or into the lumen ends to be anastomosed to provide stability and/or structure to the anastomosed lumen.

The inventor of the '699 patent, along with the other inventor of the present invention, conceived of modifications to the device which could provide advantages in certain clinical applications, as well as conceived of new advantageous uses of the device, which are described in detail below.

The device of the present invention is in the form of a tubular structure, also referred to herein as a straw-like structure. The tubular straw-like structure is impermeable and preferably composed of a biodegradable material which will degrade within the body after a period of time. The tubular structure in some embodiments provides structure and/or stability to the body lumens, e.g., forms a scaffold) and/or provides protection from leakage. The tubular structure has a thin wall and a lumen extending therethrough, and has an open top and bottom end. "Top" and "bottom" as used herein refer to orientation wherein top is closer to the patient's head and bottom is further from the patient's head. Also, top and bottom as used herein relates to direction of flow of body fluids or substances, e.g., the stool passes from the top to bottom. Proximal as used herein can also refer to the top portion and distal refer to the bottom portion, also relating to flow/passage.

The tubular structure can be formed of one piece which provides the advantages of ease of manufacture and more flexibility as opposed to the use of covered stents which need to have an impermeable cover attached to the inner structure, e.g., frame.

In some embodiments, the tubular device of the present invention is used with anastomosis of two body lumens, such as two portions of the intestine. In other embodiments, the tubular device is used in an area to be radiated to limit tissue damage. In still other embodiments, the tubular device can be used in cases of perforation, such as a perforation of the intestine secondary to diverticulitis or iatrogenic perforation, to seal the perforation. Various other clinical applications of the tubular straw-like device of the present invention are also contemplated.

Figure 1:
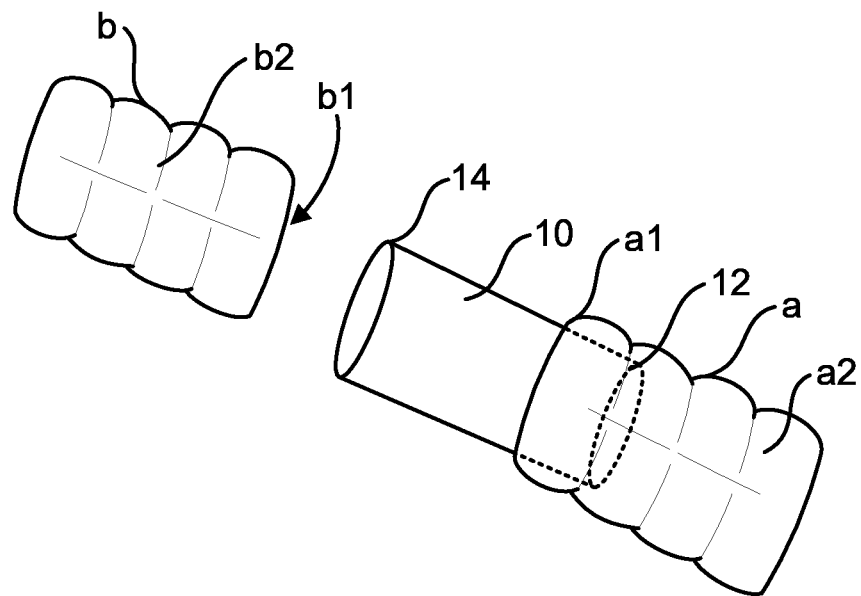
FIG. 1 is a perspective view of an embodiment of the tubular device of the present invention shown inserted into a lumen of a first intestine portion (section), the second intestine portion (section) not yet attached.
Figure 2:
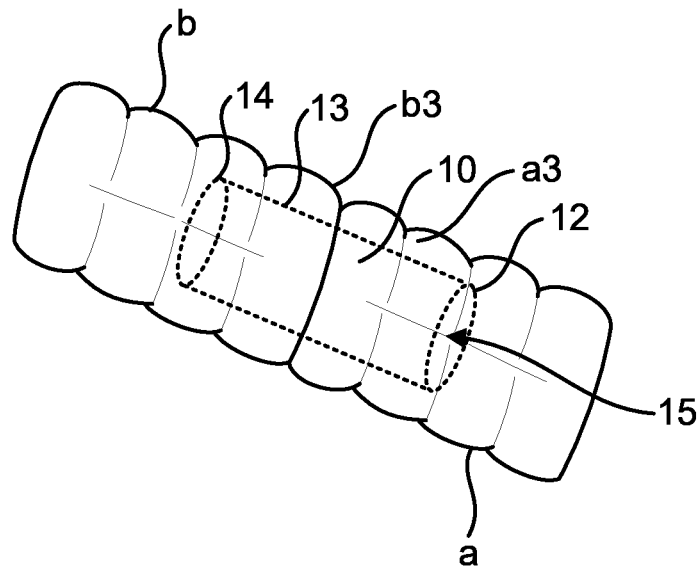
FIG. 2 is a perspective view similar to FIG. 1 showing the tubular device inserted into the lumen of the second intestine portion and the second intestine portion placed in apposition (abutment) with the first intestine portion.

Referring now to the drawings and particular embodiments of the present disclosure, wherein like reference numerals identify similar structural features of the devices throughout the several views, the device (stent) of a first embodiment of the present invention is designated generally by reference numeral 10. Device 10 is in the form of a biodegradable straw and has a first open end 12 and a second opposite open end 14. The device can have the dimensions set forth above. First end 12 is dimensioned, i.e., outer dimension, to be inserted into opening a1 and into lumen a2 of first intestine portion a and second end 14 is dimensioned, i.e., outer dimension, to be inserted into opening b1 and into lumen b2 of second intestine portion b. Thus, the ID of the lumen is greater than the OD of the device 10. FIG. 1 illustrates first end 12 of device 10 inserted into lumen portion a and not yet inserted into lumen portion b; FIG. 2 illustrates device 10 inserted into both intestine portions a, b and the portions a, b approximated and in contact (abutment) for anastomosis. The inner diameter (inner lumen 15) of device 10 is dimensioned to accommodate body fluid flow and maintain unobstructed passage through the intestine. Note the drawings of FIGS. 1-9 show a large space between the intestine wall and device for clarity since in application the device OD would be close to the lumen ID as explained below.

In use, a lumen, such as a colon, is separated and a diseased portion is removed. After removal, the surgeon inserts one end of the tubular device 10 into one end of the separated lumen (or the separated lumen end is placed over the device 10). The second end of the tubular device 10 is then inserted into the other lumen (or the lumen end is placed over the device 10), and the two lumens are attached to each other by various methods such as suturing, stapling and/or use of an adhesive to create an anastomotic site.

The tubular device 10 inserted prior to anastomosis acts as a prophylactic measure against leakage and/or soilage and prevents the inconvenience and frequent complications associated with treating leaking anastomosed lumens. Additionally, the use of the device may prevent scarring and may eliminate or reduce constrictions (strictures) caused by closure of the lumen, such as by scarring or fusion post surgery.

In some embodiments, use of device 10 may promote healing in the affected area of the lumen.

Apparatus and methods of the present inventions can be utilized for anastomosis in various lumens of the body and the intestine in FIGS. 1 and 2 is provided by way of example. Other lumens include for example lumens located in the gastrointestinal tract, the urinary tract, the cardiovascular system, the biliary tract, pancreatic duct and the genitourinary tract. Suitable anastomosis sites may include for example the intestines, esophagus, stomach, bile ducts, pancreas, pancreatic duct, ureter, pancreas and urethra. Other body lumens/tubular structures and sites are also contemplated. Uses of the device other than for anastomosis are also contemplated.

In one embodiment, resection of a portion of the GI tract such as the esophagus, stomach, colon, small intestine or large intestine may be performed on a patient under general anesthesia to remove troublesome portions of luminal tissue, such as cancerous tissue. After resection, the separated lumen ends may be anastomosed, with the device 10 positioned in the luminal tissue.

The device 10 (as well as devices 20 and 30 discussed below) is shown symmetrically shaped but asymmetrical shapes, such as the ends being of different sizes or configurations, are also contemplated as are shapes other than the cylindrical shape shown, e.g., funnel shaped, non-circular cross-section, etc. Additionally, the device may be configured for custom sizing and/or shaping to conform to the contours of the lumen.

The device is preferably non-expandable such that its transverse dimension is the same during insertion as well as during placement. However, in alternate embodiments, the device is collapsible/expandable such that it is inserted in a reduced diameter configuration and expands to a larger diameter placement configuration. Expansion can be for example by an inflatable balloon or by a phase change such as with shape memory polymeric materials or by release from a constraining member.

The device can be configured to be of a size (or expandable to a size in embodiments where the device expands) to make contact with the surrounding luminal tissue, i.e., the internal wall of the lumen, for attachment and/or support. For example, where adhesive is applied to at least part of the external surface of the device and/or at least part of the internal surface of the luminal tissue, a balloon may provide a mechanism for holding the device 10 in place while the adhesive sets.

The device 10 comprises a biocompatible, biodegradable and/or bioabsorbable material. Once in place, it may disintegrate/degrade/resorb over time (once the lumens attach), and either become absorbed into or pass through the body so invasive mechanical removal is not necessary.

The tubular structure preferably provides a continuous outer wall (without openings) to provide a sealed structure along its length.

In some embodiments, the device can be composed of tissue engineered material. For example, the device can be made of cells of an organ such as colon cells.

Figure 9:
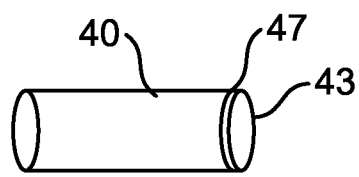
FIG. 9 is a perspective view of an alternate embodiment of the tubular device having a thickened rim portion.

In some embodiments, the device can be formed in the configuration of a condom with a rim (rib top) to providing a holding force to hold the device against the tissue/organ, e.g., colon, as shown in FIG. 9. The rim 42 of device 40 can create a radial force against the body lumen, e.g., colon, to help hold it in place. The rim, being at the top, i.e., closer to the head, could also provide a seal to prevent passage of stool behind it. An adhesive can be placed on the tip of the rim of the device to help hold it in place and provide a seal. The top of the device can in some embodiments be thicker to providing additional support as shown for example in FIG. 9. Thus, the device of FIG. 9 serves two functions: securement in place and sealing the body lumen from unwanted passage proximal of the rim 42. In this embodiment, in some instances, the adhesive need only be applied to the rim portion (top), although it is also envisioned that adhesive be applied to other regions of the device. The adhesive 43 can be applied around the rim periphery (circumference) as shown in FIG. 9. The adhesive around the rim periphery can provide the sole adhesive or alternatively adhesive could be provided on other regions.

The device 10 can include an adhesive applied thereon during the surgical procedure. The adhesive can be applied to a portion or to the entire external surface during the surgery and then the device inserted into intestinal portions as shown in FIG. 2 wherein the adhesive surface comes into contact with the inner wall of the lumen to adhesively attach the device 10 within the lumen. Note the drawings show the device not in contact with the inner wall of the lumen for clarity, it being understood, that during use the device can be configured to be of a size such that at least portions of the outer wall of the device are in contact/abutment with the inner wall of the lumen so the adhesive is pressed between the outer wall 13 of device 10 and the inner wall a3, b3 of the lumens of intestine portions a, b.

Figure 3:
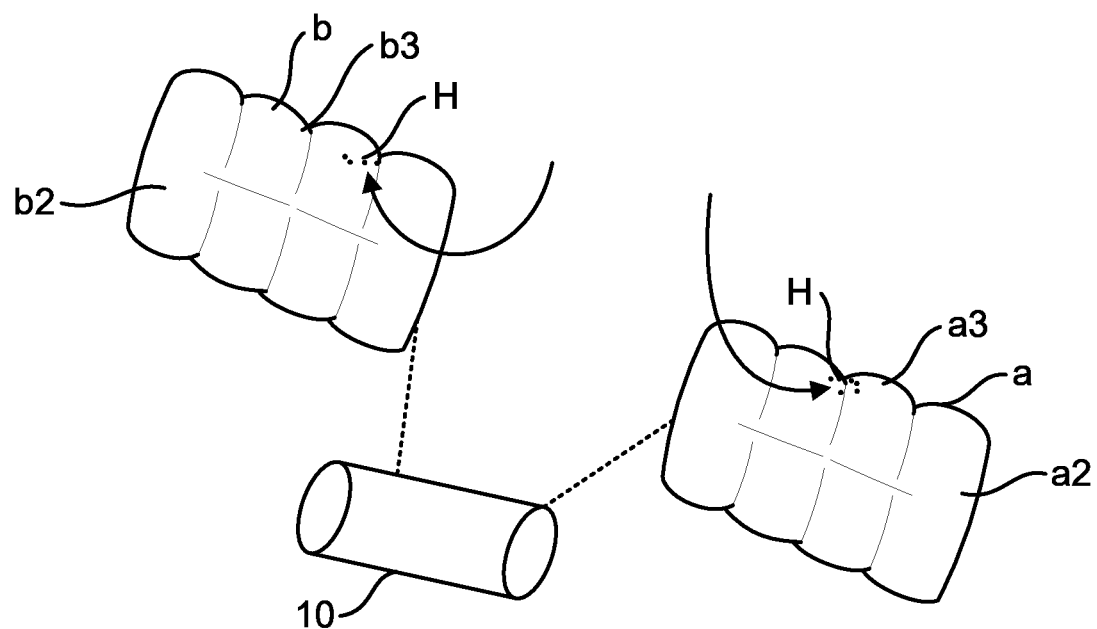
FIG. 3 illustrates an alternate embodiment wherein the adhesive is applied to the internal wall of the lumens of the intestinal portions prior to insertion of the tubular device of FIG. 1.
Figure 4:
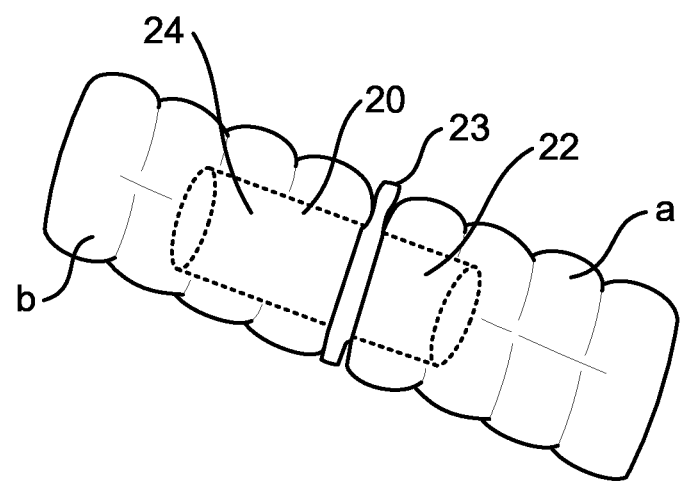
FIG. 4 is a perspective view of an alternate embodiment of the tubular device of the present invention having an enlarged region to bridge the gap between the first and second intestinal portions which are not in abutment.

In the alternate embodiment of FIG. 3, the adhesive H is applied solely to the inner wall a3, b3 of intestine portions a, b as shown schematically by the arrows. The device 10, without any adhesive applied thereto, would then be inserted into the lumens a2, b2 after such application of adhesive to adhere to the inner walls a3, b3.

The adhesive, in alternate embodiments, could be applied to device 10 prior to the surgery rather than during the surgery and then activated during the procedure. That is, the adhesive could be applied to the external wall of the device 10 prior to the surgical procedure and then activated, e.g., via warming by body temperature, or by another device or other external change, to release the adhesive to provide adherence of the device 10 to the lumen walls a3, b3.

In the embodiment of FIG. 2, the device is inserted into the lumens of the two separated intestine portions and the two portions/lumens are brought into contact/abutment for the anastomosis. In the alternate embodiment of FIG. 4, device 20 has an enlarged diameter region 23 between ends 22 and 24 at a midway portion between the two ends or alternatively closer to one of the ends. The enlarged region 23 bridges the gap between intestinal portions a, b, i.e., the portions a, b are in abutment with the enlarged region 23, on opposing sides. In some embodiments, the enlarged region 23 can have an outer diameter substantially equal to the outer diameter of portions a, b, although other outer diameters are also contemplated. In this embodiment, adhesive could also be applied to enlarged region 23 and/or sections a, b where they abut. The ends 22 and 24 are within the lumens of portions a, b and thus have a smaller OD than the ID of portions a, b. Device 20 can be made of the same material, can be of various symmetrical and asymmetrical forms, and function to provide structure in the same manner as device 10.

Figure 5:
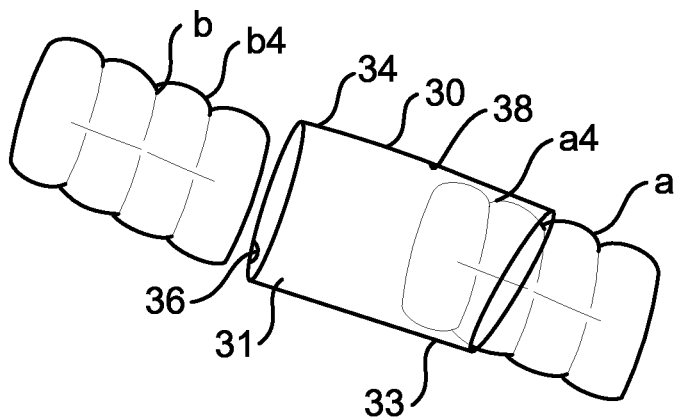
Figure 6:
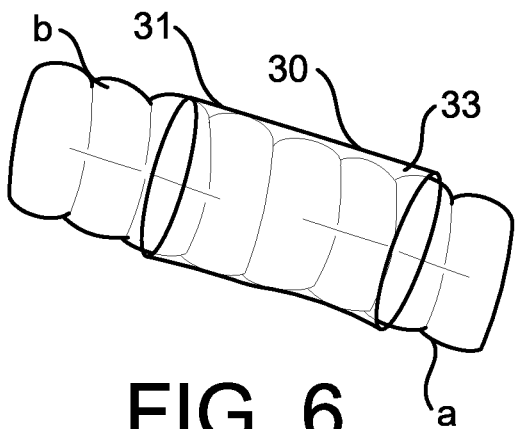
Figure 7:
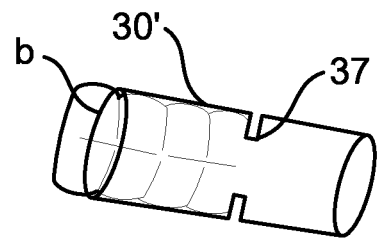
FIG. 7 is a perspective view of an alternate embodiment of the tubular device of the present invention having an inward extension.

In the alternate embodiment of FIGS. 5 and 6, device 10 is dimensioned so that it is placed over the external wall of the intestine sections a, b rather than inside the lumen of portions (sections) a, b as in FIG. 1. More specifically, device 30 has a first end 33 and a second opposite end 34 and a wall 38. The device 30 is shown in FIG. 5 placed over the outer wall a4 of intestine portion a. Intestine portion b is then received into lumen 31 of device 30 through opening 36 such that wall 38 is positioned over outer wall b4 of intestine section b. FIG. 6 illustrates the device 30 placed over both intestine sections a, b, and the sections a, b in abutment for anastomosis. As can be appreciated, in this embodiment, the inner diameter of device 30 would be greater than the outer diameter of the intestine portions a, b to accommodate the portions a, b, within its lumen 31. The device 30 could alternatively include an inwardly extending portion for positioning between the two portions a, b such that the portions a, b abut the inward extension rather than each other for anastomosis (see extension 37 of device 30' of FIG. 7).

Adhesive can be applied to the outer wall of the intestine sections a, b for attachment to the device 30. Alternatively, an adhesive can be applied to the inner wall of device 30 in lieu of adhesive application to the outer wall of sections a, b or in addition to adhesive application to the outer wall of sections a, b. Device 30 (and device 30') can be made of the same material, can be of various symmetrical and asymmetrical forms, and function to provide structure in the same manner as device 10.

In another embodiment, the devices of the present invention can include a composition to promote healing, such as a growth factor, antimicrobial agent, antibody and/or the like. Growth factors comprise cellular proteins that assist in cellular proliferation and differentiation. Antimicrobial agents, including antivirals, antibiotics and antifungals, prevent harmful bacteria, viruses and/or other microbes from infecting the anastomosed site and interfering with the tissue healing and growth processes. Certain types of antibodies may be implemented to bind with foreign objects, such as bacteria and viruses that would be harmful to the healing site if not contained, e.g., preventing strains of bacteria causing leaks. Chemotherapeutic agents can be included on the device to diffuse into the tissue site. Thus, the device in addition to preventing leaks, can serve other healing and/or treatment functions, and its biodegradable aspect avoids having to remove the device after healing or treatment.

Various uses of the devices are contemplated herein. Some examples are provided below, it being understood the devices of the present invention disclosed herein can be used in clinical applications and in other parts/regions of the body in addition to those specifically disclosed herein.

In one application, the device can be used as a scaffold (for stability and/or support) and placed across the intestine (or other body lumen) blocked by a tumor and the factor added to the device could be a chemotherapeutic to shrink the tumor.

In another application, the device could be placed across a stricture (narrowing) in the lumen of the intestine (or other body lumen) to help keep the lumen open, and the factor applied to the device could be a growth inhibitor. In some embodiments, the growth inhibitor could be low grade chemotherapeutic agent used as an anti-proliferation type drug to inhibit growth, such as paclitaxel.

Figure 8:
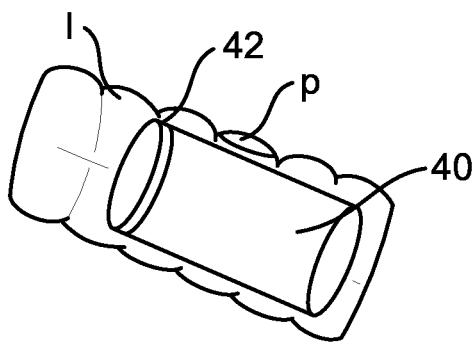
FIG. 8 is a perspective view showing the tubular device inserted into a body lumen to seal a perforation in the lumen.

In another application, the device can be used in perforation of the intestine secondary to diverticulitis or iatrogenic perforation to seal a perforation. Antibiotics can be attached to the device in some embodiments. The device can also be used to seal perforations in other body lumens/parts. FIG. 8 illustrates an example of the device 10 used to seal a perforation P in intestine I by way of example. Perforations naturally occur due to a variety of causes such as diverticulitis, ulcers, endoscopic procedures, etc. The biodegradable stent of the present invention can protect the perforation via a non-invasive (minimally invasive) method so invasive surgery is not required.

In another application, the device be used in an area to be radiated to limit tissue damage. Thus, it can add integrity to the tissue site. This may enable radiation to start sooner since the device provides a support for previously weakened tissue.

Examples of clinical/surgical applications for the devices of the present invention are disclosed in commonly owned provisional application serial nos. 63/404,202 filed on Sep. 7, 2022, 63/452,193 filed on Mar. 15, 2023, 63/452,194 filed on Mar. 15, 2023 and 63/452,197 filed on Mar. 15, 2023. The entire contents of each of these applications are incorporated herein by reference. These applications describe uses of the device at anastomotic sites as well as uses of the device not at anastomotic sites, e.g., at perforations, at tissue regions weakened by radiation, at narrowing or blocked regions of lumens, etc.

Adhesives according to various aspects of the present invention may comprise any suitable material to attach, adhere and/or bond to living tissue. Adhesives may comprise natural, naturally derived and/or synthetic materials. The adhesive may comprise a gel, liquid and/or solid. Examples of adhesives that can be used include purified bovine serum albumin and glutaraldehyde, (sold commercially as Bioglue® by Cryolife Technology, Inc., Kennesaw Georgia). The adhesive can comprise polyethylene glycol, sold commercially as Duraseal® Sealant by Confluent Surgical, Inc., Waltham, Massachusetts pr Tiseel fibrin sealant. The adhesive applied could also be Puragel or Puracif.

In preferred embodiments, the adhesive utilized not only performs an adherence function but also forms a sealing function. This dual function helps to prophylactically prevent leaks. Sealant surgical glue is one possible material that can be used.

Suitable methods of application of the adhesive may include spraying, topical application and/or injection. In one embodiment, a more viscous adhesive, such as Duraseal® Sealant, may be applied to decrease the setting time, thereby decreasing the time required for a surgeon to hold the ends of lumen together or the ends of a lumen against the device (scaffold). The adhesive may provide both a mechanism for attachment of lumen ends to each other after anastomosis, as well as a sealant to inhibit leakage after reattachment. As described above, the adhesive may bond the device to the lumen ends and may seal the connection between the device and lumen ends to inhibit leakage. In yet another embodiment, the adhesive may be applied over the device and the lumen ends to both bond the lumen ends to the device, as well as provide a seal to inhibit leakage.

In one embodiment, once a biocompatible, biodegradable and/or bioabsorbable adhesive is in place it may be configured to disintegrate, degrade and either become absorbed into or pass through the body. For example, in an application where the lumen ends are configured to heal and reseal themselves, the adhesive may no longer be necessary to bond and/or seal the lumen, and it may desirable for the adhesive to be removed.

In alternate embodiments, a suture can be used in addition to or in lieu of the adhesive to help secure the device in place. The suture can be for example in the form a "T" that hooks in place. It can be placed in various regions of the device such as at the rim in devices like those of FIG. 9 having a rim. Tacking devices can be used in addition to or in lieu of the adhesive to help secure the device in place.

The devices of the present invention can be used in various methods. In one method to prevent leakage in an intestine, the method includes a) positioning a tubular straw like device across a lumen of the intestine for positioning across an anastomotic site; and b) securing the device to the intestine utilizing an adhesive, the device including a healing or treatment substance adhered thereto. In another method to prevent leakage in an intestine, the method includes a) positioning a tubular straw like device in a lumen of a first intestinal portion to be attached to a second intestinal portion at an anastomotic site, the tubular straw having a rim with an enlarged diameter; and b) securing the device to the intestine utilizing an adhesive, the rim blocking stool passage past the rim. In another method, the device is used to seal a perforation in a body lumen, the method comprising a) positioning a tubular straw like device in the body lumen, the device having a rim having an enlarged diameter to provide a radial force against the intestine; and b) securing the device to a wall of the body lumen utilizing an adhesive, the rim preventing backflow past the rim. In another method to protect an intestine during radiation, the method includes a) positioning a tubular straw like device in a lumen of a first intestinal portion, the tubular straw having a rim with an enlarged diameter; and b) securing the device to the intestine utilizing an adhesive, the rim blocking stool passage past the rim.

Figure 17:
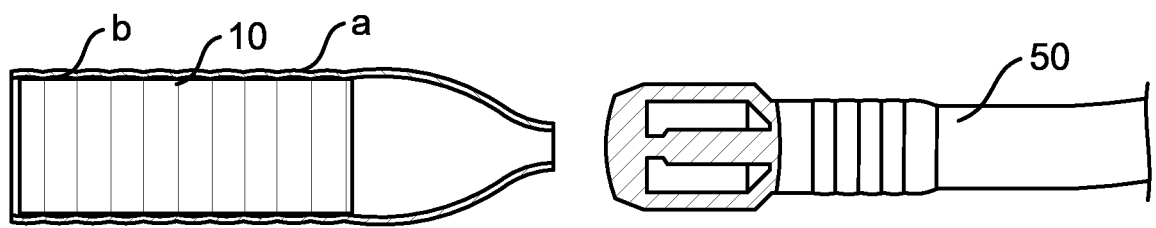
Figure 18:
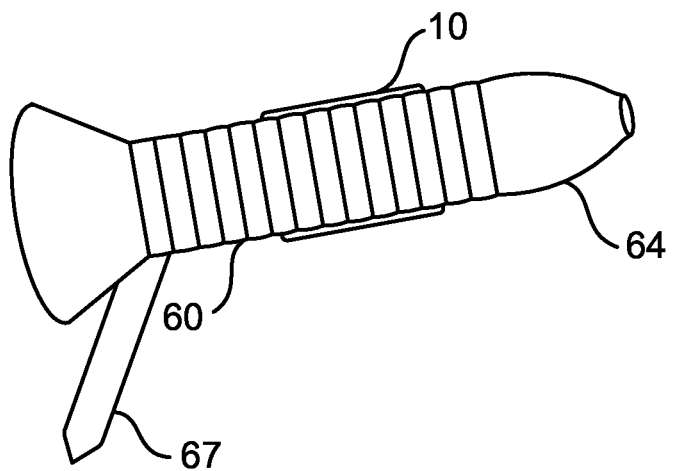
FIG. 18 illustrates an alternate embodiment of the delivery system of the present invention utilizing a proctoscope to deliver the leak protection device.
Figure 19:
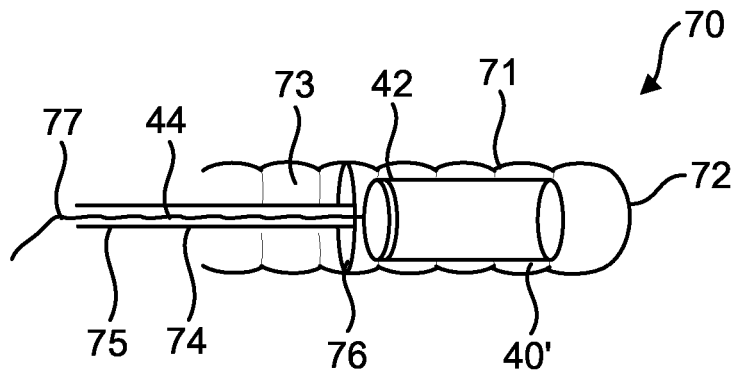
Figure 20:
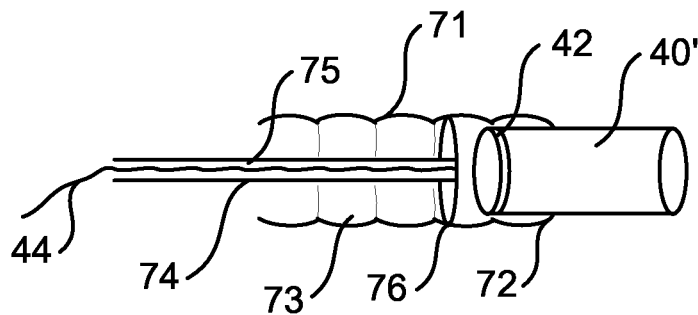
Figure 21:
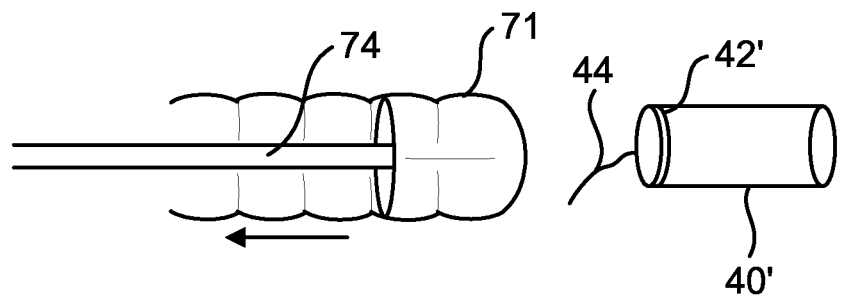

Turning now to the delivery systems of the present invention for delivering the tubular devices of the present invention, FIGS. 12-21 illustrate various embodiments wherein FIGS. 10-17 illustrate delivering the tubular device utilizing an anastomosis device such as a circular stapling device, e.g., an EEA device, which carries the tubular device externally (outside) on the shaft; FIG. 18 illustrates delivering the tubular device utilizing a proctoscope which carries the tubular device externally on its body; and FIGS. 19-21 illustrate delivering the tubular device via an outer delivery member in which the tubular device is positioned. Each of these embodiments are described in detail below. Note that the delivery devices are shown delivering one of the embodiments of the leakage protection devices of the present invention; however, it should be understood that the device can be used for delivering any of the devices disclosed herein and used in any of the various methods disclosed herein and is not limited to leakage protection.

Figure 12:
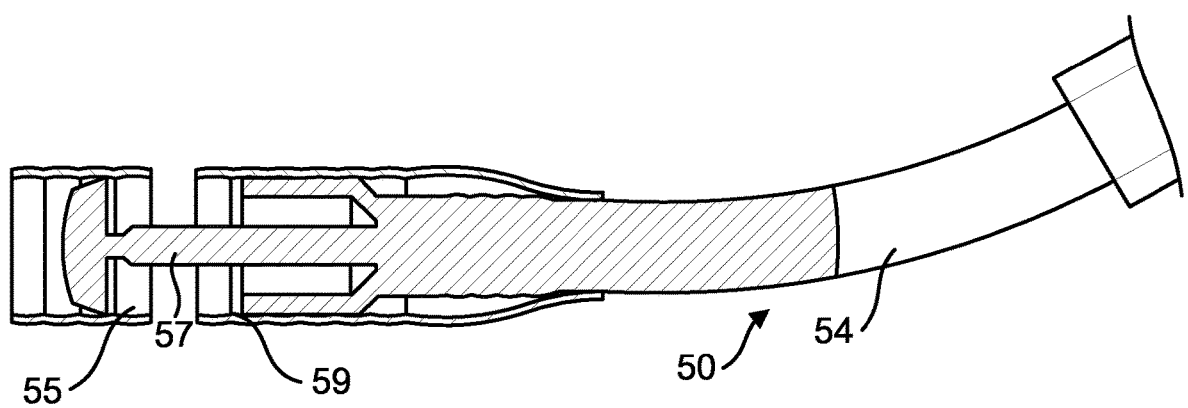
Figure 13:
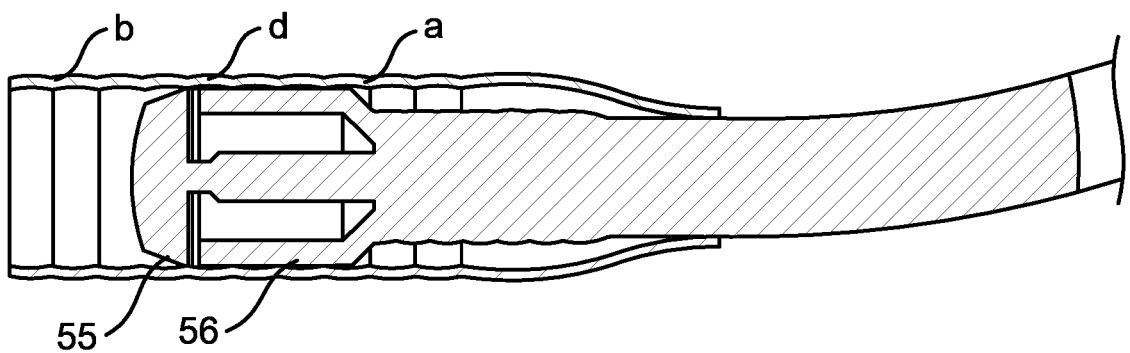

Turning first to the embodiment of FIGS. 10-17, the tubular device 10 is delivered by a circular stapling/circular anastomosis instrument. The stapling instrument (stapler) is designated generally by reference numeral 50 and has a shaft 52 and a stapler/anvil head 56 positioned at the distal end of the shaft 52. Head 56 has a stapling portion or head 59 containing circular arrays of staples and an anvil 55 supported by and movable by an anvil shaft 57 (FIG. 12). The anvil shaft 57 is movable via rotation knob 58 to move the anvil 55 in distal and proximal directions to open the head 56 and to close the head 56 to approximate tissue for retention between the stapler head 59 and anvil 55. The staples are advanced against the anvil surface of anvil 55 for formation thereof. Handle or lever 53 is actuable to advance a firing member to fire (deploy) the staples from stapler head 59.

The device 10 (or other leak protection devices disclosed herein) is supported on an outer surface of the instrument shaft 52. As shown, it is supported adjacent the handle portion of the instrument but could be supported on other regions of the stapler shaft 52. After the anastomosis is performed by the stapler 50, the device 10 on that same anastomotic stapler 50 is advanced by an external pusher (not shown) so it can be slid down the shaft 52 to the anastomotic site. Once at the site, the stapler 50 is removed, leaving the device 10 at the site to prevent leakage as described herein.

Figure 10:
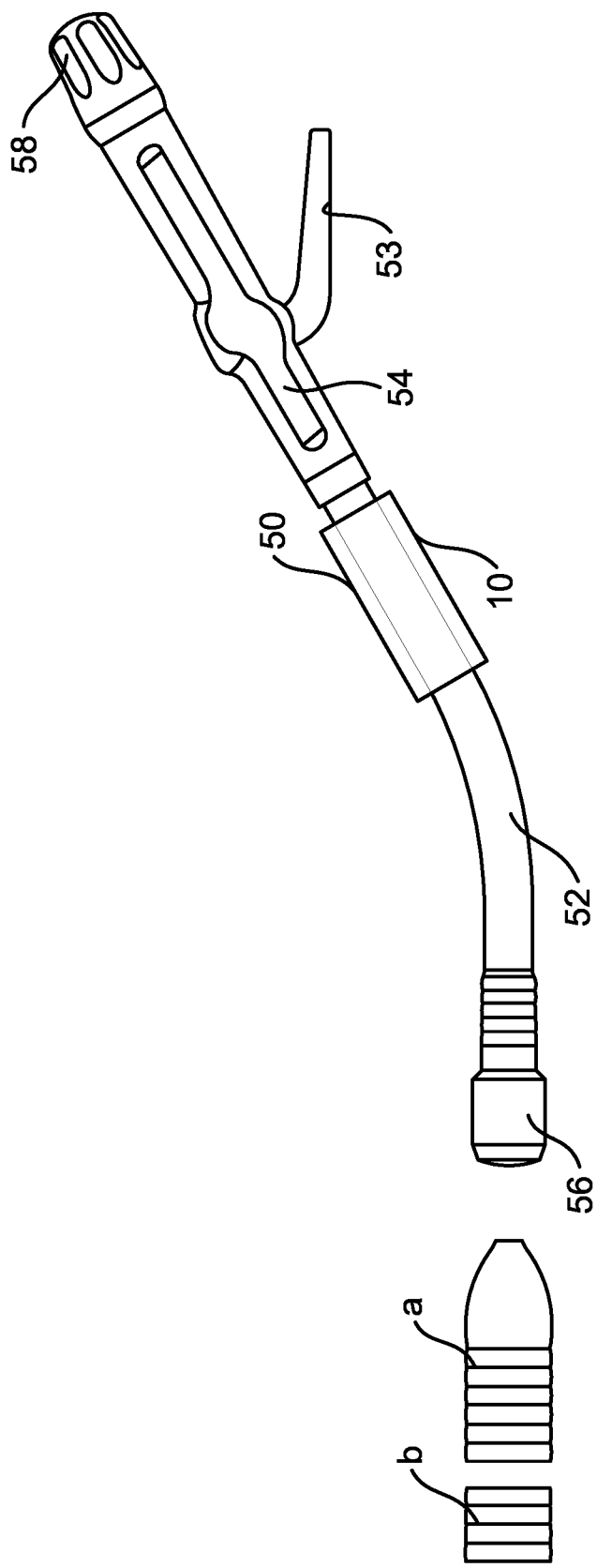
Figure 11:
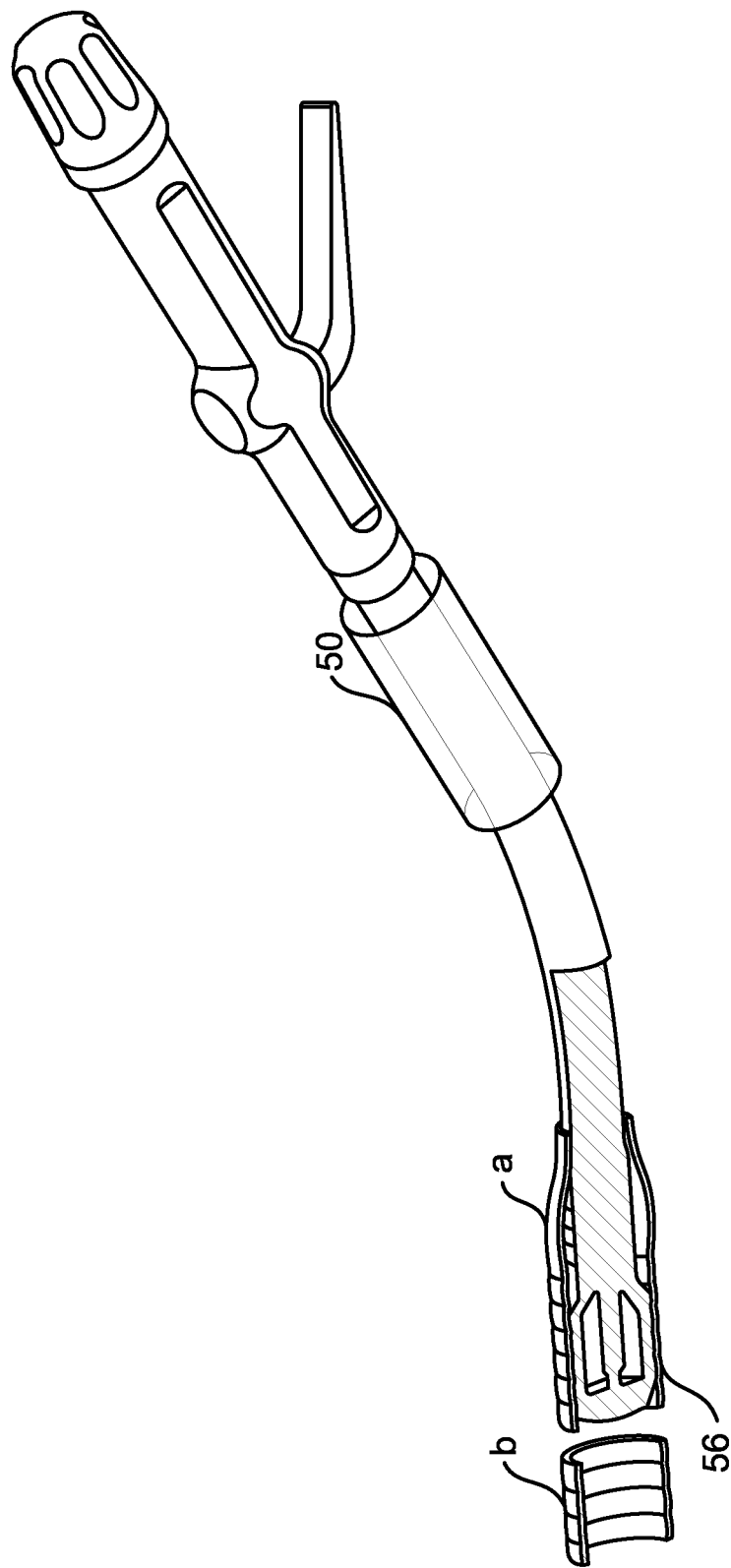

The method steps will now be described in conjunction with FIGS. 10-17. The stapler 50 is shown in FIG. 10 prior to insertion into the rectum/colon. The intestinal portions a and b are shown unattached and ready for attachment. The tubular device 10 is supported on shaft 52 spaced proximally of the stapler head 56. The distal portion of the instrument 50 is inserted into the rectum and advanced toward the defect in the colon (see arrow of FIG. 11). Next, the stapling instrument 50 is opened by rotation of knob 58 to move anvil 55 via anvil shaft 57 distally to space it from the stapler head 59 as shown in FIG. 12. The anvil 55 is then approximated toward stapler head 56 to clamp the intestinal end portions therebetween, and a circular array(s) of staples are advanced from the staple head 59 through tissue via actuation of lever 53 to repair the defect (FIG. 13), e.g., to attach the two intestinal portions at an anastomotic site d.

Figure 14:
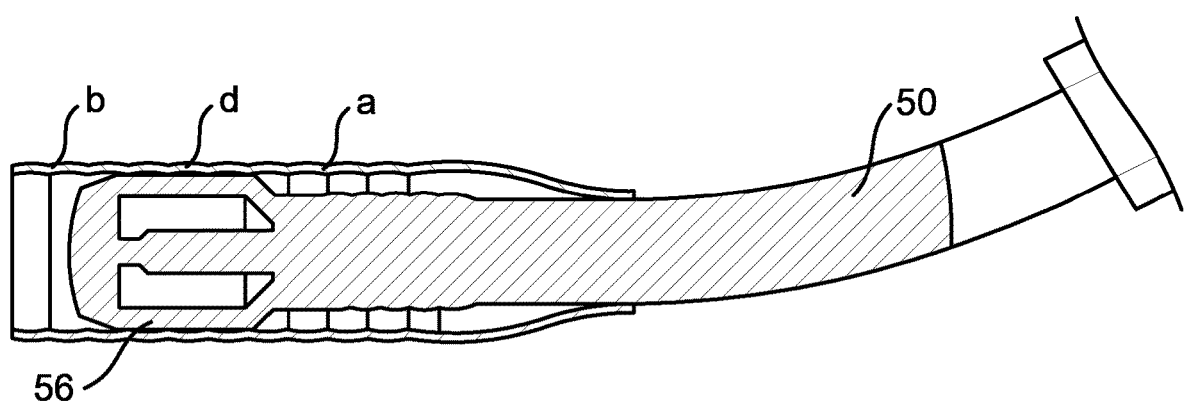
Figure 15:
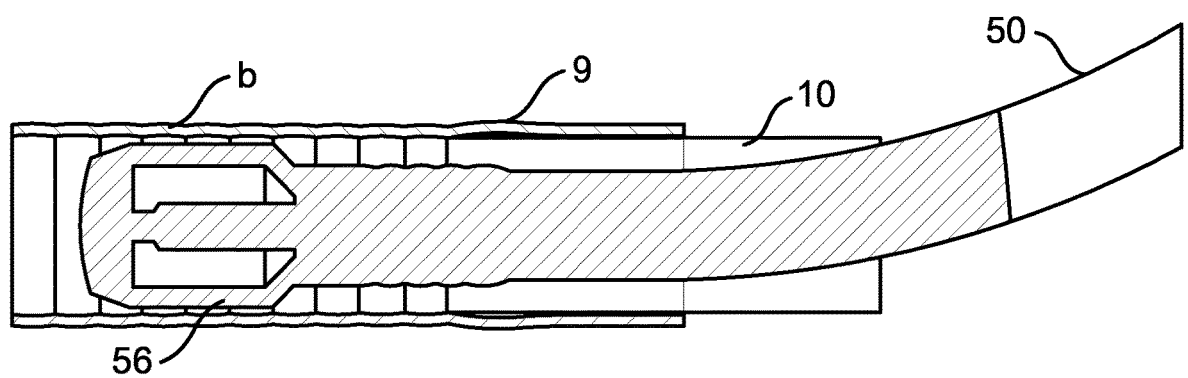
Figure 16:
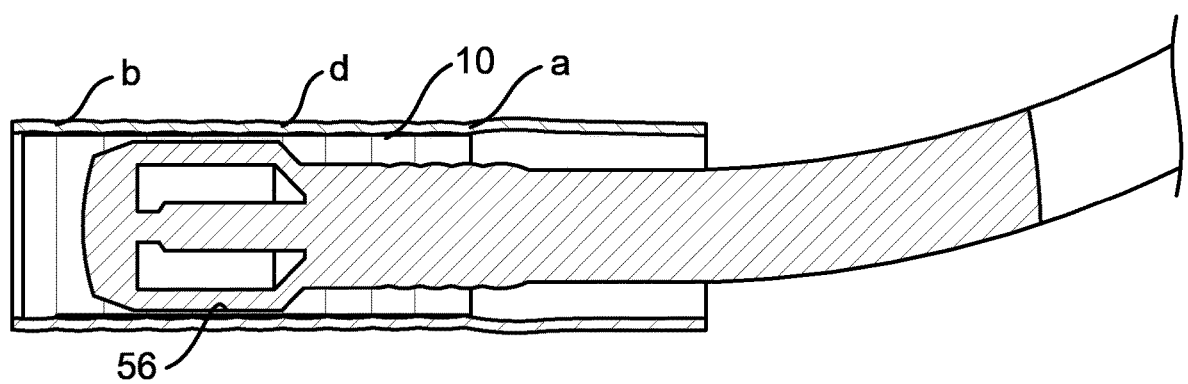

The instrument 50 is next advanced further into the colon so the staple head 59 is centered over the repair site d as shown in FIG. 14. Next, the leak protection device 10 is advanced distally along the outer shaft into the rectum (FIG. 15). Note a pusher (not shown) could be utilized to advance the device 10 into the rectum. Note the pusher can be part of the instrument 50 or a separate device.

Once the device 10 is delivered to a position wherein it is centered at the repair site d, (FIG. 16), the instrument 50 is removed leaving the device 10 inside the colon centered at the repair site (FIG. 17). By having the device 10 pre-mounted on the instrument which performs the anastomosis, e.g., on a circular stapler such as an EEA instrument or on a suturing or other type of stapling instrument, it avoids the extra step of having to go back into the colon with a delivery device such as rigid proctoscope to deliver the leak protection device. Note alignment markers can be provided on the instrument and/or the tubular device to aid in centering the instrument head 56 and/or tubular device 10 at the anastomotic site.

FIG. 18 illustrates an alternate embodiment of the delivery system of the present invention wherein the tubular device 10 (or other leak protection devices disclosed herein) is mounted externally to a body portion of a proctoscope 60. Proctoscope 60 has a handle 62 and a tapered distal end 64 for ease of insertion. The tubular device 10 is carried by the proctoscope 60 to the target site and then advanced distally over the body of the proctoscope 60 and over the distal end (tip) 64 for delivery to the target site. The device 10 can be advanced over the proctoscope 60 by a pusher (not shown) which can be part of the proctoscope 60 or a separate device.

FIGS. 19-21 disclose an embodiment of the delivery system wherein the device 40 (or other leak protection devices disclosed herein) is delivered internally rather than externally as in the embodiment of FIGS. 12 and 18. More specifically, delivery system 70 includes an outer delivery member 71 (also referred to herein as a delivery sheath) having a tapered end portion 72 which is smooth and atraumatic. The body of delivery member 71 can be of uniform diameter along its length or alternatively can taper in either a distal direction so a proximal portion has a larger diameter than a distal portion or taper proximal in a proximal direction. Slidable axially within the outer delivery sheath 71 is a pusher member 74. The pusher member 74 is preferably connected to the delivery sheath 71 so although it slides within a lumen 73 of the sheath 71 it cannot come out of the sheath 71. This can be achieved by attachment or by stops on the pusher and/or in the lumen 73. Pusher 74 has a pusher head 76 which in the illustrated embodiment is enlarged relative to the shaft of the pusher 74 which contacts a proximal end of the tubular device 10 and advances the device 10 out from the confines of the delivery member 71.

The tubular device 40' shown in FIGS. 18-21 is similar to the tubular device of FIG. 8 in that it has an enlarged rim 42'. Note the device can be positioned so the rim 42' is engaged by the pusher head 76 as shown or alternatively positioned within the delivery member in the opposite direction so the rim 42' is at the distal end of the delivery member 71 and not engaged by the pusher head 76. Tubular device 40' differs from device 40 in that it has a retrieval string 75 extending proximally from the body. The string 75 can be attached to an inner or outer wall of the device 40', preferably at a proximal region. Note a retrieval string like string 75 can be provided in the tubular devices of the other embodiments disclosed herein. The retrieval string 75 enables quick removal of the tubular device if needed such as in emergency situations by pulling (tensioning) the string proximally.

Turning now to the method of use of delivery system 70, the device 40' is positioned within lumen 73 of delivery member 71. In this position, it is within the confines of the delivery member 71 and delivered to the target site, e.g., site of a defect, e.g., an anastomotic site. In this position, the pusher 74 is in a retracted (more proximal) position and the string 44 of the device 40' extends through the lumen 75 of pusher 74, extending out the proximal opening 77 of the lumen 75 of pusher 74.

The delivery member 71 is advanced into the rectum and colon, i.e., through lumens in the two intestinal portions, such as intestinal portions a and b of the aforedescribed drawings. When ready for delivery, the pusher 74 is advanced in the direction of the arrow (FIG. 20) so that pusher head 76 engages a proximal end of device 10 and pushes it out the distal end. Note the distal end 72 of delivery member 71 can separated/spread (FIG. 20) as the device 10 is forced through it. This can be achieved by formation of the distal tip by a plurality of individual fingers which when closed create a seal and can be forced open by a force applied by the device 40' as it is forced through by pusher 74. Other forms of closed/sealed frangible tips, e.g., with perforations, can also be utilized. FIG. 21 illustrates the device 40' fully exposed for placement and securement at the target site and the delivery system 70 being removed in the direction of the arrow.

Note the delivery devices are described above for use with leak protection devices, however, the delivery devices can also be used to deliver other devices disclosed herein and for other methods, i.e., other clinical uses.

Although the apparatus and methods of the subject invention have been described with respect to preferred embodiments, those skilled in the art will readily appreciate that changes and modifications may be made thereto without departing from the spirit and scope of the present invention as defined by the appended claims. Persons skilled in the art will understand that the various embodiments of the disclosure described herein and shown in the accompanying figures constitute non-limiting examples, and that additional components and features may be added to any of the embodiments discussed herein without departing from the scope of the present disclosure.

It will be understood by those skilled in the art that the above particular embodiments are shown and described by way of illustration only. The principles and the features of the present disclosure may be employed in various and numerous embodiments thereof without departing from the scope and spirit of the disclosure. The above-described embodiments do not restrict the scope of the disclosure.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the present disclosure, terms such as "approximately," "about", "generally," "substantially," and the like should be understood to allow for variations in any numerical range or concept with which they are associated. It is intended that the use of terms such as "approximately", "about", "substantially", and "generally" should be understood to encompass variations on the order of 25%, or to allow for manufacturing tolerances and/or deviations in design. For example, the term "generally parallel" should be understood as referring to configurations in which the pertinent components are oriented so as to define an angle therebetween that is equal to 180°±25% (e.g., an angle that lies within the range of (approximately) 135° to (approximately) 225°).

The recitation of numerical ranges by endpoints includes all numbers within the range.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A method to prevent leakage of an intestine and/or provide support to an intestine, the method comprising:
 a. advancing an anastomotic instrument comprised of a stapling device deploying at least one annular array of staples through a first intestine portion and a second intestine portion, the anastomotic instrument carrying a tubular straw like device on an outer wall of a shaft of the instrument, the tubular device formed as one piece and having a first end opening, a second end opening and a lumen extending through an entire length of the device;
 b. actuating the instrument to attach the first intestine portion to the second intestine portion to form an anastomotic site;
 c. after step b, advancing the tubular device distally over the shaft of the instrument into a lumen of the first intestine portion and the second intestine portion;
 and d. securing the device to the first intestine portion such that an outer wall of the device extends across the anastomotic site.

2. The method of claim 1, wherein the step of securing the device comprises the step of securing the device utilizing an adhesive.

3. The method of claim 1, wherein the device includes a treatment or healing substance adhered thereto.

4. The method of claim 1, wherein a pusher advances the device over the shaft of the instrument.

5. The method of claim 1, further comprising the step of centering a stapling head of the instrument at the anastomotic site and delivering the tubular device so it is centered at the site.

6. The device of claim 5, wherein one or both of the instrument or device have alignment markers to aid in centering the device.

7. The method of claim 1, wherein the tubular device has a first diameter and a rim having a second diameter larger than the first diameter, and adhesive is placed on the rim, the rim preventing backflow through the rim and the rim providing a radial force against the intestine.

8. The method of claim 1, wherein the device is formed of tissue engineered material.

9. The method of claim 8, wherein the tissue engineered material comprises colon cells.

10. A method to prevent leakage of an intestine or provide support to the intestine, the method comprising
 a. advancing an instrument comprised of a proctoscope through a first intestine portion and a second intestine portion, the instrument carrying a tubular straw like device on an outer wall of the instrument, the tubular device formed as one piece and having a first end opening, a second end opening and a lumen extending through an entire length of the device;
 b. advancing the tubular straw like device distally over the outer wall of the instrument into a lumen of the first intestine portion and the second intestine portion;
 and c. securing the device to the first intestine portion such that an outer wall of the device extends across the anastomotic site.

11. The method of claim 10, wherein the step of securing the device comprises the step of securing the device utilizing an adhesive.

12. The method of claim 10, wherein a pusher advances the device over the shaft of the instrument.

13. A method to prevent leakage of an intestine or provide support to the intestine, the method comprising
 a. advancing an instrument through a first intestine portion and a second intestine portion, the instrument having a lumen retaining a tubular straw like device therein, the tubular device formed as one piece and having a first end opening, a second end opening and a lumen extending through an entire length of the device;
 b. advancing the device through the lumen of the instrument exiting a distal end of the instrument and into a lumen of a first intestine portion and the second intestine portion;
 c. securing the device to the first intestine portion such that an outer wall of the device extends across the anastomotic site; and
 d. applying a healing or treatment substance to an outer wall of a rim of the device prior to insertion into the first intestine portion, the substance applied at least at a region adjacent the region adjacent an anastomotic site.

14. The method of claim 13, wherein the instrument includes a pusher therein, the pusher is advanceable to advance the tubular device out of the lumen of the instrument.

15. The method of claim 13, wherein a distal tip of the instrument separates to enable passage of the device through the distal tip and into the first intestine.

16. The method of claim 13, wherein the tubular device includes a string extending proximally thereof to enable retrieval of the device after delivery.

17. The method of claim 13, wherein the device is formed of tissue engineered materials.

* * * * *